United States Patent [19]
Lobdell et al.

[11] 4,193,004
[45] Mar. 11, 1980

[54] FLUID LEVEL MONITORING THROUGH FLUID CELL PROTRUSION

[75] Inventors: Donn D. Lobdell, Golden; Stephen J. Herman, Evergreen; Robert L. Anderson, Boulder; Thomas E. Goyne, Denver, all of Colo.

[73] Assignee: Cobe Laboratories, Inc., Lakewood, Colo.

[21] Appl. No.: 917,850

[22] Filed: Jun. 22, 1978

[51] Int. Cl.² ............................................. G01N 21/26
[52] U.S. Cl. ...................................... 250/577; 73/293
[58] Field of Search .............. 250/573, 574, 575, 577; 73/293; 356/244, 246

[56] References Cited
U.S. PATENT DOCUMENTS

| | | |
|---|---|---|
| 2,882,520 | 4/1959 | Hass . |
| 3,065,354 | 11/1962 | Bird . |
| 3,549,893 | 12/1970 | Gibbs .................................. 250/577 |
| 3,636,360 | 1/1972 | Oishi et al. . |
| 3,851,181 | 11/1974 | Heule . |

*Primary Examiner*—David C. Nelms

[57] ABSTRACT

Monitoring the level of both opaque and clear liquids in a reservoir without contacting the liquids by providing first and second reservoir wall portions that define a region through which a light beam is passed from a light source to a light sensor so that opaque liquid extinguishes the light beam and so that the wall portions cooperate with the clear liquid to refract the light beam away from the sensor. A monitoring line segment, defined as the portion of a hypothetically unrefracted and unreflected light beam between the first and second reservoir wall portions, is a small fraction of the largest interior linear dimension of the reservoir in a plane containing the monitoring line segment and a line normal to the first reservoir wall portion.

17 Claims, 5 Drawing Figures

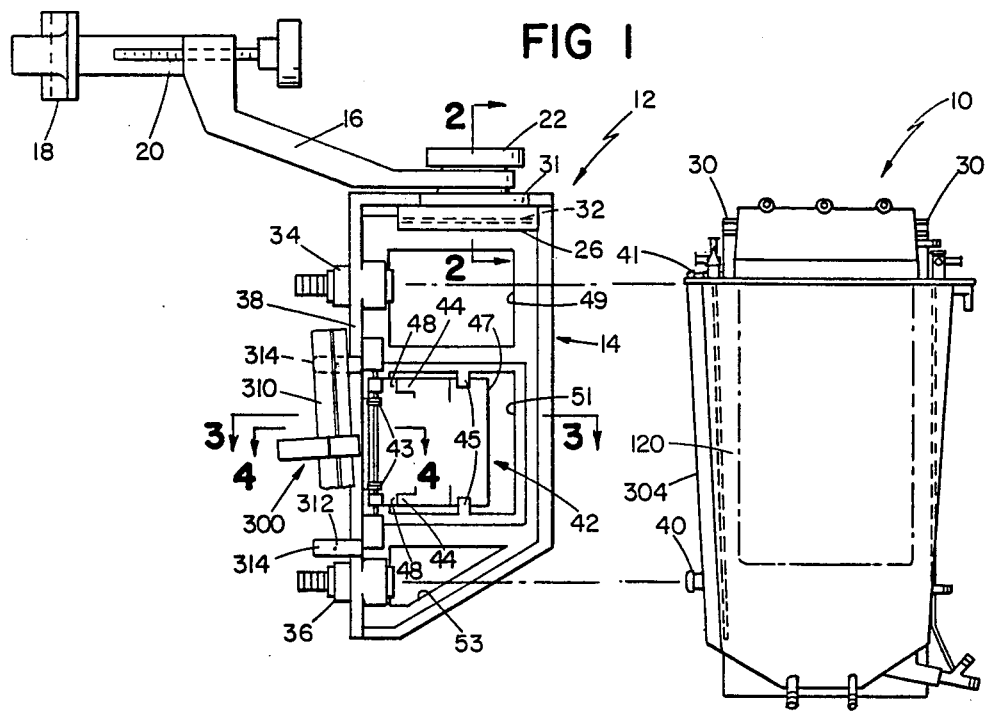
FIG 1
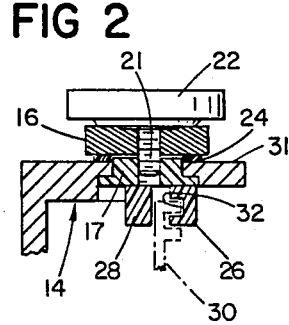
FIG 2
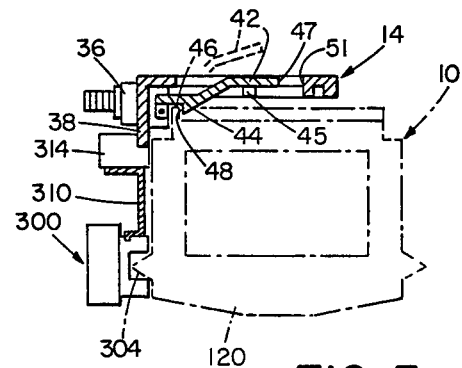
FIG 3
FIG 4

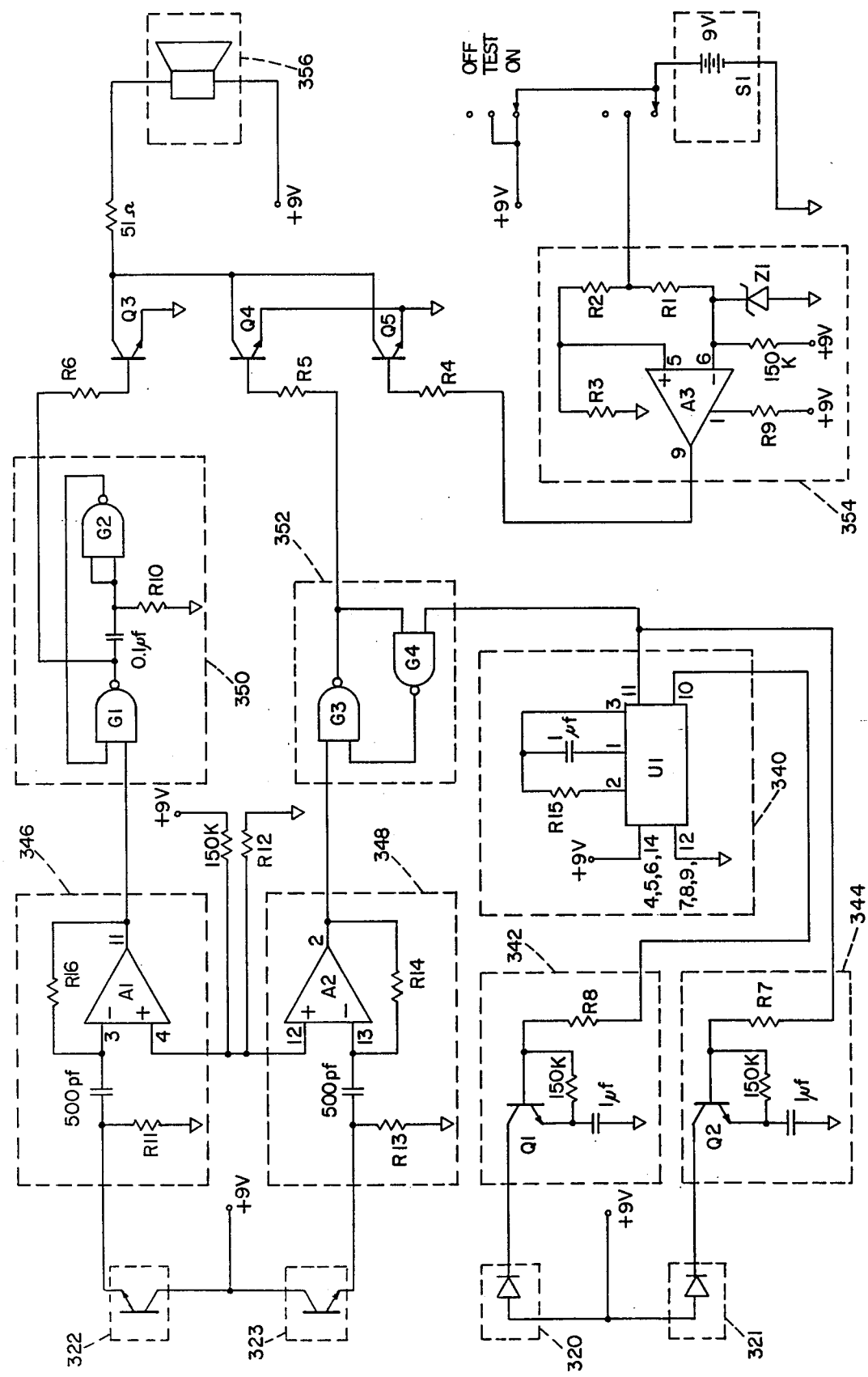

FLUID LEVEL MONITORING THROUGH FLUID CELL PROTRUSION

FIELD OF THE INVENTION

This invention relates to optical fluid level monitors, particularly those for monitoring the level of clear fluids.

BACKGROUND OF THE INVENTION

It is sometimes desirable to be able to automatically monitor the level of both opaque and clear liquids without contacting the liquids. For example, in a blood oxygenator the damgerous consequences of allowing the blood level to fall too low in the arterial blood reservoir—infusion of gas into the patient—makes it highly desirable to monitor blood level. Optical monitors provide a sterile (no fluid contact) means to do so, but correct operation of the level monitor in an oxygenator is best confirmed before blood is introduced by monitoring the level of a clear saline priming solution.

Oishi et al. U.S. Pat. No. 3,636,360 shows monitoring the liquid level of a pressure vessel by passing a light beam from a bulb centrally through a transparent tube communicating with and positioned vertically alongside the vessel and relying on the difference in relative refractivity between a wall-to-air interface and a wall-to-liquid interface to cause the light beam to emerge from the tube along different paths so as to only activate a phototransistor when air occupies the monitored portion of the tube. It is mentioned that opaque liquid filling the tube will prevent light from reaching the sensor and that the bulb and phototransistor, shown supported in separate projector and receiver housings mounted on a flat plate, could be adjusted vertically. In one embodiment the transparent tube is triangular in cross section.

Bird U.S. Pat. No. 3,065,354 shows a liquid level monitor contained within a sealed tube extending downward into a reservoir. Collimated light is passed through a prism one surface of which is exposed to the reservoir. Depending on whether liquid or gas occupies the monitored level, light is refracted at the exposed surface along one of two paths, then reflected by a mirror facing the prism, and finally viewed through a window by a photoconductive cell, the window being positioned along only one of the two light paths.

Heule U.S. Pat. No. 3,851,181 shows a blood level monitor for an oxygenator. The monitor has a plurality of sensors spaced vertically along one transparent wall. Each sensor uses a pair of LED's emitting flashing 1000 Hertz infrared light to illuminate the reservoir and a single phototransistor to sense light reflected by the blood.

Hass U.S. Pat. No. 2,882,520 teaches a level detection means based on light absorption for detecting the height of a column of mercury.

SUMMARY OF THE INVENTION

We have discovered that the level of both opaque and clear liquids in a reservoir can be monitored without contacting the liquids by providing an integrally-formed transparent monitoring portion in the reservoir having first and second wall portions that define a region smaller than the full reservoir through which region a light beam is passed from a light source to a light sensor so that opaque liquid extinguishes the light beam and so that the wall portions cooperate with the clear liquid to refract the light beam away from the sensor. In preferred embodiments, the first and second wall portions protrude from a wall of the reservoir and extend upwardly; the wall portions form a triangle in cross section; the light source and sensor are supported in a housing which straddles the upwardly-extending protruding position; a monitoring line segment, defined as the portion of a hypothetically unrefracted and unreflected light beam between the first and second reservoir wall portions, is less than 1/10 of the largest interior linear dimension of the reservoir in a plane containing the monitoring line segment and a line normal to the first reservoir wall portion; and the light beam flashes on and off so that it can be distinguished from ambient light. Applied to an oxygenator, our invention allows a continuous monitoring of liquid level from the very start of oxygenation, when clear priming solution is being introduced into a patient's blood. As the liquid in the oxygenator becomes more opaque as blood follows the clear priming solution through the oxygenator, monitoring continues without need for operator adjustment.

PREFERRED EMBODIMENT

The structure and operation of the preferred embodiment of the invention are as follows:

STRUCTURE

The drawings show the preferred embodiment and related apparatus, which are then described.

1. DRAWINGS

FIG. 1 is an elevation view of a blood oxygenator being inserted into its mount, the level monitor being shown supported on the mount (a portion of the mounting plate for the level monitor is cut away);

FIG. 2 is a fragmentary sectional view taken through 2—2 of FIG. 1;

FIG. 3 is a fragmentary sectional view taken through 3—3 of FIG. 1, showing the level monitor engaged with the oxygenator (the latter shown in broken lines);

FIG. 4 is a fragmentary sectional view taken through 4—4 of FIG. 1 with the blood oxygenator installed, showing the level monitor; and FIG. 5 is a schematic view of the level monitor electronics.

2. DESCRIPTION

Turning to FIG. 1, there is shown blood oxygenator 10 being inserted into aluminum supporting mount 12. The mount has back brace 14 from which extends arm 16. At the end of arm 16 is formed V-shaped gripping portion 18 which cooperates with screw 20 to grasp a mounting post (not shown). Arm 16 is rotatably fastened to back brace 14 by nylon bearing 17 (FIG. 2), to which the arm is attached by two screws (not shown). Knob 22 turns screw 21 threaded into nylon bearing 17 to squeeze arm 16 and brace 14 against nylon lock washer 24 to lock the arm in any angular position in relation to the brace.

Below the arm-to-brace connection are nylon track portions 26, 28 (FIG. 2), which receive lip 30 on the top of oxygenator 10 and are secured to horizontal shelf 31 on brace 14. Track portion 26 has groove 32. Brass water couplings 34, 36 secured in vertical wall 38 by set screws (not shown) receive plastic inlet fitting 40 and outlet fitting 41 on oxygenator 10. Internal O-rings (not shown) in the brass couplings seal between the couplings and fittings. Back plate 42, which is biased by torsion springs 43 against stops 45 and which has ramp portions 44 (FIG. 3), captures tab 46 on the back of oxygenator 10 in grooves 48 at the ends of the ramp portions. Openings 49, 51, 53 are provided in the brace. Back plate 42 swings through opening 51 into which stops 45 protrude. Level monitor mounting plate 310 fastened to bosses 314 supports level monitor 300. Oxygenator 10 is constructed entirely of clear polycarbonate plastic (such as Lexan, a General Electric trademark) except where noted, and individual pieces are adhered by solvent bonding or by a polyurethane adhesive. Blood collects in reservoir 120, which has along one wall vertically-extending protruding ridge 304, which is straddled by portions of level monitor 300 (FIG. 3). Further details regarding the construction and operation of an oxygenator, the blood level in which can be monitored by fluid level monitor 300, may be found in the copending U.S. patent application of Donn D. Lobdell and Stephen J. Herman entitled "Gas Exchange Apparatus", the contents of which are hereby incorporated by reference herein.

The level of blood collecting in reservoir 120 is monitored by optical level monitor 300, which passes two parallel, vertically-spaced (⅜ inch) light beams along paths 302 (both appear as one path in FIG. 4) through vertically-extending protruding ridge 304 (triangular in the sectional view of FIG. 4). The length of the segment of path 302 inside ridge 304 is a small fraction (less than 1/10 here and preferably less than ¼) of the largest interior horizontal dimension of reservoir 120.

The level monitor has U-shaped optics housing 305 (machined polycarbonate) and attached electronics housing 306. Both housings are supported by spring clip 308 tightened against mounting plate 310 by screw 311. The mounting plate is fastened to mount 12 by screws (not shown) received in threaded holes 312 in bosses 314, and is tilted from the vertical to be parallel to ridge 304. Groove 316 in optics housing 305 receives lip 318 on the mounting plate.

Vertically-spaced (⅜ inch) light emitting diode (LED) sources 320, 321 emit flashing light beams seen by phototransistor sensors 322, 323 (only upper source 320 and upper sensor 322 are shown in FIG. 4). The LED's and phototransistors are recessed ⅛ inch from surfaces 324, 326 in blind holes 328 and 330 (0.2 inch diameter). Surfaces 324, 326 are spaced 1 inch apart to clear ridge 304, which is ⅝ inch wide at its base, and has 0.10 inch thick equal-length walls 332, 334 angled 55° from the reservoir wall.

Turning to FIG. 5, there is shown a schematic for the level monitor electronics. Multivibrator 340 generates a pair of 4 hertz square wave outputs which are supplied to transistor stages 342, 344, which drive upper and lower LED sources 320, 321 (OP132W, Optron Incorporated, Carrollton, Texas) with exponentially decaying current pulses about 10 milliseconds long. Light reaching upper and lower phototransistor sensors 322, 323 (OP803, Optron Incorporated, Carrollton, Texas) sends an input signal to AC-coupled amplifiers 346, 348, respectively. The output of amplifier 346 controls one-shot flip-flop 350; the output of amplifier 348 cooperates with an output of multivibrator 340 to control set/reset flip-flop 352. Outputs of the two flip-flops and an output from battery level sense circuit 354 drive 400 Hertz audio alarm 356 (Al105, Projects Unlimited, Dayton, Ohio) through power transistors Q3, Q4, Q5. The low frequency of the alarm helps in localizing the oxygenator as the source of the noise in an operating room.

The following table identifies the circuit components shown in FIG. 4, except for those resistors and capacitors whose values are given in the Figure:

| | Component Table |
|---|---|
| A1–A3 | Siliconix L144CJ |
| G1–G4 | Motorola MC14011 |
| U1 | RCA CD4047 astable multivibrator |
| Q1–Q5 | National Semiconductor LM3086 |
| R1–R8 | Allen Bradley 316B242 (2.4K ohm) |
| R9–R16 | Allen Bradley 316B105 (1M ohm) |
| Z1 | 1N746 Zener diode |
| S1 | Mallory MN1604 (9V) battery |

Operation

The electronics shown in FIG. 5 provides an audible alarm whenever the fluid level (blood or clear priming solution) falls below the level at which level monitor 300 is set. The vertical position of the monitor can be manually adjusted by sliding housings 305, 306 vertically on mounting plate 310. Friction between clip 308 and mounting plate 310 retains the housings at any selected vertical position, and lip 318 and groove 316 guide the housings during adjustment.

A drop in fluid level below the monitor level is sensed by a rise in the intensity of light seen by phototransistor sensors 322, 323. When the intensity rises to 5 percent of the maximum intensity (the intensity achieved when light passes through a clean dry portion of ridge 304), amplifiers 346, 348 generate an output which causes flip-flops 350, 352 to activate 400 Hertz audio alarm 356. As the fluid level drops, upper sensor 322 is the first to sense the rise in light intensity, and it causes a 4 Hertz chirping of the 400 Hz alarm. If the fluid level drops further to below lower sensor 323, the alarm sound becomes an intermittent 400 Hertz tone.

Contamination of the interior surfaces of walls 332, 334 with either a thin film of blood or water condensation can reduce light transmission to 10 percent of maximum intensity, but will still trigger the alarm. However, if blood is allowed to dry on walls 332, 334 in the region monitored, enough light from both LED sources 320, 321 can conceivably be blocked by individual dried drops of blood to cause the monitor to malfunction. Providing two vertically spaced pairs of sources and sensors reduces the likelihood of this occurrence and also provides component redundancy to improve reliability.

When blood fills ridge 304 above the monitoring level, all light generated by the LED sources is absorbed. But when clear priming liquid is above the monitoring level, light refraction, rather than absorption, is relied on to extinguish the light intensity at sensors 322, 323. Light is refracted generally along paths 360, away from the sensors. Light leaving sources 320, 321 along paths 302 is bent inward 10° by the difference in refractivity between air and the priming solution (some bending of the light also occurs in walls 332, 334). The refracted beam strikes wall 334 at a 45° angle and is bent a further 25°, leaving ridge 304 along a path bent inward 35°. Light paths 302, 360 represent the paths of perfectly collimated light emitted by LED sources 320, 321. Because the sources actually emit light in a cone, there being a 50% reduction in light intensity at 12° off axis, some light follows different paths from those shown. Some light undergoes total internal reflection and never exits from wall 334, but enough reaches sensors 322, 323 to produce about 1 percent of maximum intensity there, well below, however, the 5 percent threshold for turning on the alarm.

Other Embodiments

One upwardly-extending corner of reservoir 120 could substitute for protruding ridge 304. Optics housing 305 would then straddle the corner instead of the ridge. Further, the alarm triggered by the lower optical monitor could be made a continuous rather than intermittent 400 Hz tone.

Other Inventions

Subject matter disclosed herein relating to the mount for the oxygenator was the joint invention of Thomas E. Goyne, Stephen J. Herman, Joel F. Giurtino and Robert L. Anderson.

Incorporation by Reference

We incorporate by reference the copending U.S. patent application of Donn D. Lobdell and Stephen J. Herman entitled "Gas Exchange Apparatus".

What is claimed is:

1. Apparatus for monitoring the level of a liquid in a reservoir, comprising:
   an integrally-formed transparent monitoring portion of said reservoir, said monitoring portion including
   a first transparent wall portion and
   a second transparent wall portion,
   a light source positioned outside of said reservoir for directing a beam of light toward said first wall portion along a first linear path,
   said first linear path passing through said wall portions and defining a monitoring line segment as that portion of said first linear path inside said wall portions,
   said monitoring line segment being a small fraction of the largest interior dimension of a monitoring cross section taken through said reservoir along a plane defined by said first linear path and an intersecting line normal to said first transparent wall portion, and
   a light sensor positioned outside said reservoir and directed at said second transparent wall portion along a second linear path,
   said second linear path being the path said beam of light takes upon exiting from said second wall portion when said monitoring portion is not occupied by liquid,
   said first and second wall portions being adapted when said monitoring portion is occupied by liquid to cause said beam of light transmitted by said source to be refracted within said monitoring portion and to emerge from said second wall portion along a third linear path not striking said sensor.

2. The apparatus of claim 1 wherein said first and second wall portions have thicknesses less than ¼ the length of said monitoring line segment.

3. The apparatus of claim 1 wherein said first and second wall portions define an upwardly-extending corner of said reservoir.

4. The apparatus of claim 1 wherein said first and second wall portions define an upwardly-extending protruding portion of a wall of said reservoir.

5. The apparatus of claim 4 wherein said protruding portion has a triangular horizontal cross section, sections of said first and second wall portions forming two legs of said triangular cross section.

6. The apparatus of claims 3 or 4 wherein the vertical position of said light sensor and source are adjustable for providing adjustment in the monitoring level.

7. The apparatus of claim 4 wherein said light source and sensor are supported in a housing which straddles said upwardly-extending protruding portion.

8. The apparatus of claim 7 wherein said housing is upwardly adjustable for providing adjustment in the monitoring level.

9. The apparatus of claim 1 wherein said beam of light flashes on and off for distinguishing said beam from ambient light.

10. The apparatus of claim 7 wherein said source and sensor are recessed within holes in said housing.

11. The apparatus of claim 1 further comprising a second light source and a second light sensor vertically spaced apart from said first-mentioned source and sensor, said second source and sensor for providing redundancy in the event said first source and sensor fail to operate.

12. The apparatus of claim 1 wherein said monitoring line segment is less than ¼ the length of the largest interior dimension of said monitoring cross section.

13. The apparatus of claim 12 wherein said monitoring line segment is less than 1/10 the length of the largest interior dimension of said monitoring cross section.

14. A reservoir for holding a light transmissive liquid having a refractive index different from that of air, said reservoir comprising:
   at least one wall for containing said liquid,
   an integrally-formed transparent monitoring portion of said wall, said monitoring portion including
   a first transparent upwardly extending wall portion protruding outwardly from said wall,
   a second transparent upwardly extending wall portion protruding outwardly from said wall,
   said first and second wall portions adapted to bend by refraction a beam of light directed along a path between said wall portions when light transmissive liquid occupies the path, for thereby deactivating a light sensor positioned along said path outside of said reservoir.

15. The reservoir of claim 14 wherein said first and second protruding wall portions together have a triangular cross section, sections of said first and second wall portions forming two legs of said triangular cross section.

16. The reservoir of claim 15 wherein said triangular cross section has the shape of an isosceles triangle, sections through said first and second walls forming legs of equal size.

17. The reservoir of claim 15 wherein the angle between said first and second portions is 70°.

* * * * *